(12) United States Patent
Haas

(10) Patent No.: US 7,090,859 B2
(45) Date of Patent: Aug. 15, 2006

(54) KETOPROFEN COMPOSITIONS AND METHODS OF MAKING THEM

(76) Inventor: Ronald Thomas Haas, 6 Sayre Dr., Princeton, NJ (US) 08540

( * ) Notice: Subject to any disclaimer, the term of this patent is extended or adjusted under 35 U.S.C. 154(b) by 347 days.

(21) Appl. No.: 10/319,301

(22) Filed: Dec. 13, 2002

(65) Prior Publication Data

US 2004/0116528 A1 Jun. 17, 2004

(51) Int. Cl.
*A61K 9/00* (2006.01)
*A61K 9/14* (2006.01)

(52) U.S. Cl. ............... 424/400; 424/484; 424/489
(58) Field of Classification Search ............... 424/1
See application file for complete search history.

(56) References Cited

U.S. PATENT DOCUMENTS

| | | | |
|---|---|---|---|
| 3,228,831 A | 1/1966 | Nicholson et al. | |
| 3,385,886 A | 5/1968 | Nicholson et al. | |
| 3,641,127 A | 2/1972 | Farge et al. | |
| 4,534,980 A | 8/1985 | Itoh et al. | |
| 4,545,992 A * | 10/1985 | Kamishita | 514/161 |
| 4,844,907 A * | 7/1989 | Elger et al. | 424/465 |
| 4,861,797 A * | 8/1989 | Haas | 514/557 |
| 5,654,337 A | 8/1997 | Roentsch et al. | |
| 5,776,505 A | 7/1998 | Maasz et al. | |
| 5,866,162 A * | 2/1999 | Grattan | 424/466 |
| 5,914,129 A * | 6/1999 | Mauskop | 424/464 |
| 6,184,220 B1 * | 2/2001 | Turck et al. | 514/226.5 |
| 2002/0169212 A1 | 11/2002 | Stroble et al. | |

FOREIGN PATENT DOCUMENTS

| | | |
|---|---|---|
| DE | 3328401 A1 | 2/1985 |
| EP | 0418564 A1 | 3/1991 |
| EP | 0510246 A1 | 10/1992 |
| EP | 0672422 A1 | 9/1995 |
| EP | 0698393 A | 2/1996 |
| WO | WO 89/03210 | 4/1989 |
| WO | WO 96/16017 | 5/1996 |
| WO | WO 97/24114 | 7/1997 |
| WO | WO 98/22083 | 5/1998 |
| WO | WO 99/52528 | 10/1999 |
| WO | WO 01/49276 A2 | 7/2001 |
| WO | WO 01/49276 A3 | 7/2001 |

OTHER PUBLICATIONS

"Glycerin". Dictionary.com. Online. Internet. Accessed on Feb. 13, 2006. <http://dictionary.reference.com/search?q=glycerin>.*
"Hydrocodone". The Merck Index. Online. Internet. Accessed on Feb. 10, 2006. <http://themerckindex.cambridgesoft.com>.*
"Glycerol". The Merck Index. Online. Internet. Accessed on Feb. 13, 2006. <http://themerckindex.cambridgesoft.com>.*
Hildebrand et al, "Characterisation of ketoprofen sodium solutions, HPC gels and liquid crystals as potential topical formulations," European Journal of Pharmaceutical.
Science, vol. 4, Suppl., 1996, p. S43.
Hildebrand et al, "Ketoprofen Sodium: Preparation and Its Formation of Mixed Crystals with Ketoprofen," Journal of Pharmaceutical Sciences 1997, vol. 86, No. 7, pp. 854-857.
Rote Liste Service GMBH (ED): "Rote liste 2002, Ketoprofen 100 von ct Amp (05308)," Jun. 14, 2002, p. 05308.
Database WPI, Section Ch, Week 199246, Derwent Publications, AN 1992-376272 and JP04275235A (Hisamitsu Pharm), Sep. 30, 1992.
Database WPI, Section Ch, Week 198445, Derwent Publications, AN1984-279244 and JP59172419A (Suzuki M), Sep. 29, 1984.
Database WPI, Section Ch, Week 199303, Derwent Publications, AN1993-021388 and JP04346916A (Iwaki Pharm), Dec. 2, 1992.

* cited by examiner

*Primary Examiner*—Carlos Azpuru
*Assistant Examiner*—Casey Hagopian
(74) *Attorney, Agent, or Firm*—Eugene S. Indyk

(57) ABSTRACT

A wide variety of pharmaceutically and commercially acceptable dosage forms of ketoprofen are prepared by dissolving ketoprofen in pharmaceutically acceptable solvents.

1 Claim, No Drawings

KETOPROFEN COMPOSITIONS AND METHODS OF MAKING THEM

TECHNICAL FIELD

This invention relates to ketoprofen and to compositions and formulations involving ketoprofen.

BACKGROUND

Ketoprofen is a nonsteroidal composition that has long been recognized as being useful in the treatment of pain, inflammation, and fever. More particularly, ketoprofen has been found in clinical studies to be very effective in the treatment of the signs and symptoms of rheumatoid arthritis, osteoarthritis, mild to moderate pain, fever, and primary dysmenorrhea, among other things. Ketoprofen is at least as effective as other available high potency compounds, such as indomethacin and phenylbutazone, but without their attendant side effects, such as increased toxicity. Also, ketoprofen is obtainable over the counter in certain dosages, whereas other high potency compounds are not.

There currently are no liquid or semi-solid ketoprofen products available on the market. There is, however, a great unfulfilled need for a liquid or semi-solid analgesic having fever reducing and anti-inflammatory properties which is safe, effective, and capable of being formed into a pharmaceutically elegant product. Three compositions tried in the past are aspirin, acetaminophen, and ibuprofen. Applicant has identified several disadvantages in using these compositions as compared with using ketoprofen. First, the analgesia produced by a given amount of aspirin, acetaminophen, or ibuprofen is less than that produced by the same amount of ketoprofen. Second, acetaminophen compositions lack anti-inflammatory activity. Third, aspirin compositions produce significant gastrointestinal distress in some patients. Fourth, aspirin has been reported linked to Reye's syndrome in children. Fifth, acetaminophen has been reported to cause liver failure in some patients and has been more recently been questioned about its possible link to renal disorders. Sixth, although ibuprofen could be a drug of choice, ketoprofen in lower dosages has the same positive effect as ibuprofen; also, ibuprofen can involve gastrointestinal side effects, although less than those associated with aspirin. Furthermore, it has come to the Applicant's attention that in children and infants, there is a need for a fever reducing composition with the benefit of an anti-inflammatory effect.

Although ketoprofen has significant advantages over aspirin, acetaminophen, and ibuprofen, there are notable problems in preparing satisfactory dosage forms of ketoprofen. This is because ketoprofen is insoluble in water, has very bitter taste, and is unstable in aqueous media. Applicant has essentially solved all of these problems by finding a way to dissolve ketoprofen in pharmaceutically acceptable solvents and make pharmaceutically acceptable liquid and semisolid dosage forms of ketoprofen. For example, Applicant has developed a method of preparing and using alkali metal salts of ketoprofen to create novel dosage forms of ketoprofen. These salts are easily dissolved in water, they permit preparation of pharmaceutical compositions which are virtually lacking in the unpleasant taste sensations of ketoprofen, and they are stable in aqueous media. They are more easily absorbed by the body and they involve less gastrointestinal distress than conventional anti-inflammatory compositions.

Dosages of ketoprofen have been available in the market place only in solid form such as in a tablet or a capsule form. There are significant segments of the population, however, who are unable to conveniently take medication in solid form. These include the pediatric population, the geriatric population, the infirm, and those who for whatever reason cannot or prefer not to swallow solid dosages of medication. For these people, the benefits of ketoprofen have been effectively unavailable because of the unavailability of liquid or semisolid forms of the composition. Until this time, attempts to meet the needs of these people involved use of other analgesic compositions in liquid forms such as liquid acetaminophen. The acetaminophen compositions lack anti-inflammatory activity, however. Aspirin has come into disfavor because it causes gastrointestinal discomfort in some patients and it reportedly has been linked to Reye's syndrome in children.

Efforts to create liquid formulations of 2-arylproprionic acids such as ketoprofen, allegedly through the "salification" of ketoprofen in aqueous vehicles, have been a failure. The formulations created have been so unstable that the constituents of the formulation must be kept physically separate until the time of administration to the patient or they must be kept away from light in an inert atmosphere such as nitrogen, helium, argon, or mixtures of two or more such inert gases. See U.S. Pat. No. 5,895,789.

Applicant has invented a number of beneficial ibuprofen compositions. His U.S. Pat. No. 4,859,704 refers to various liquid ibuprofen formulations and his U.S. Pat. No. 4,861, 797 refers to various compositions involving the alkali metal salt of ibuprofen. These patents, however, do not show or suggest the novel ketoprofen compositions and dosage forms and the processes of making them disclosed and claimed in this application.

SUMMARY

Applicant has solved the problems noted above by creating pharmaceutically and commercially acceptable dosage forms of ketoprofen that can be prepared by dissolving ketoprofen in pharmaceutically acceptable solvents. For example, a novel water soluble form of ketoprofen may be prepared by reacting ketoprofen and an alkali metal bicarbonate in a aqueous medium. This procedure permits the preparation of a number of novel formulations, which result in pharmaceutically and commercially acceptable dosage forms. For example, a clear, stable, and palatable liquid ketoprofen can be prepared. A process of making such a ketoprofen composition is significantly simpler and less expensive to carry out than prior processes of making liquid ketoprofen compositions. The liquid ketoprofen composition may also contain pharmaceutically acceptable alcohol, dispersing and suspending agents, viscosity increasing agents, flavorings, sweetening agents and preservatives. Other liquid or semi-solid ketoprofen dosage forms may also be prepared by dissolving ketoprofen compositions in pharmaceutically acceptable solvents. These compositions and formulations are useful in treating pain, inflammation, and fever in mammals.

One of the objects of the invention is to provide a novel ketoprofen composition, particularly the alkali metal salt of ketoprofen.

It is also an object of the invention to provide a method of making those novel ketoprofen compositions, particularly a method that is simple and economical and uses readily available materials.

It is a further object of the invention to provide a ketoprofen composition which avoids the problems of prior ketoprofen compositions and preserves the benefits of those ketoprofen compositions.

It is an additional object of the invention to make novel formulations resulting in pharmaceutically elegant and commercially viable liquid and semi-solid dosage forms of ketoprofen.

It is yet another object of the invention to create formulations which require less of an amount of active ingredient to achieve a given therapeutic effect.

It is a further object of the invention to provide a novel liquid and semi-solid ketoprofen compositions and novel methods of making those compositions.

It is yet a further object of the invention to provide novel liquid and semi-solid ketoprofen compositions which are simpler and more economical to make than any such compositions proposed in the past.

It is an additional object of the invention to provide a liquid ketoprofen which is clear and chemically and physically stable.

It is yet an additional object of the invention to provide a ketoprofen composition in which the control of pH is not a critically important factor.

It is another object of the invention to provide a liquid ketoprofen composition which does not need hydrophilic emulsifying agents or colloidal clays to disperse and suspend the ketoprofen in a liquid medium.

It is an additional object of the invention to provide a liquid ketoprofen composition which does not need to use antioxidants.

It is an additional object of the invention to provide an alkali metal salt liquid dosage forms of ketoprofen such as injectables, topical solutions, topical solution patches, oral rinses, sprays, nasal sprays, dental sprays and other dosage forms. The ketoprofen salts can also be used to formulate semi-solid dosage forms such as suppositories, soft gelatin capsules, ointments, creams, gels, and other dosage forms. Furthermore, solid dosage forms such as capsules, conventional tablets, lozenges, chewable tablets, quick dissolving tablets, and others may be prepared.

It is a further object of the invention to provide a ketoprofen composition that can be combined with other active ingredients, such as narcotics, antihistamines, anti-infectives, antibiotics, decongestants, and other medications.

Other objects and advantages are either specifically described elsewhere in the application or are apparent from the description in the application.

In accordance with these objects and advantages, a composition of matter is disclosed and claimed. In one representative example of the invention, that composition comprises a ketoprofen composition dispersed and suspended, or dissolved, in an aqueous medium. Also in accordance with these objects and advantages, a method of making such a composition is disclosed and claimed.

One additional example of the invention involves an alkali metal salt of ketoprofen. The salt may be prepared by dissolving a predetermined amount of an alkali metal bicarbonate in an aqueous medium and then dissolving a predetermined amount of ketoprofen in the aqueous medium containing the bicarbonate composition.

An additional example of the invention would be certain dosage forms such as gels, creams, and ointments of ketoprofen made by dissolving ketoprofen in pharmaceutically acceptable solvents such as pharmaceutically acceptable alcohols.

DETAILED DESCRIPTION

Novel and pharmaceutically elegant dosage forms of ketoprofen may be prepared by dissolving a ketoprofen composition in a pharmaceutically acceptable solvent. One particularly notable dosage form of ketoprofen in accordance with this invention is a clear, colorless, stable, and palatable liquid ketoprofen. Liquid ketoprofen compositions in accordance with the invention may contain a therapeutically effective amount of the alkali metal salt of ketoprofen dispersed, suspended, and dissolved in an aqueous medium. Specific examples of liquid compositions may contain an amount of ketoprofen salt which is the mass equivalent of approximately 12.5 to 150 mg of ketoprofen per 5 ml sample of the composition. Exemplary dosages of ketoprofen salt within the range set forth above include those having a mass equivalent of about 12.5 mg, 25 mg, 50 mg, 75 mg, and 150 mg of ketoprofen per 5 ml of the composition (about two tablespoons).

A bicarbonate composition is added to an aqueous medium to assist in the dispersion of the ketoprofen during the formulation of the composition. A suitable bicarbonate composition is an alkali metal bicarbonate, such as sodium or potassium bicarbonate. Potassium bicarbonate is preferred. Normally, bicarbonate compositions are used to adjust pH, but it is used in these compositions to disperse the ketoprofen in the medium and help it go into solution. The amount to be used is determined in empirical studies of the amounts needed to produce a desired amount of dispersion and dissolution. Those studies indicate that on the order of a 2.5 grams of ketoprofen for each gram of potassium bicarbonate promotes the rapid and complete dissolution of ketoprofen into the aqueous medium resulting in a clear and stable ketoprofen solution without any solid or particulate matter evident upon visual examination. Also, the extremely bitter and burning taste of ketoprofen is substantially eliminated in these ketoprofen liquids.

It may, however, be desirable to mask even the small residual remnants of the flavor of ketoprofen. This may be accomplished by the addition of one or more flavoring agents. One of these flavoring agents may be sweetener, such as sorbitol or sucrose, which may be added to the medium not only to mask the unpleasant flavor of the ketoprofen, but also to increase the viscosity of the composition so that a syrup results. To enhance the stability and shelf life of ketoprofen compositions of this invention, and to produce a haze free composition, it is suggested that, if sucrose is used, it be a high purity sugar. An example of such sucrose is Bottler's Grade Extra Fine, No Floc, sold by Holly Sugar.

Some patients may not be able to tolerate high levels of sucrose. In that case, an artificial sweetener may be used in the invention of this application instead of sucrose. Such artificial sweeteners include sodium saccharine and aspartame. If these sweeteners are used, however, it may be desirable to add a composition such as glycerol, sorbitol, propylene glycol, or combinations of two or more of those ingredients in an amount which will build up the viscosity of the resulting composition.

In addition to sweetening the composition of the invention to mask the flavor of the ketoprofen, other ingredients may be added to enhance its flavor and mouth feel. One possibility is menthol; another is glycerin. Glycerin also may be used to increase the viscosity of the composition. Fruit flavorings may also be added to the composition, such as banana, berry or citrus fruit flavorings. Licorice, bubble gum, selected spices, such as cinnamon, and a mint, such as peppermint, may also be used to flavor the liquid ketoprofen composition. The flavorings may be natural and/or artificial. Commercially available flavoring systems from flavor houses such as Firmenich may be employed.

Compositions in accordance with this example of the invention of this application are liquid ketoprofen compositions exhibiting a great deal of clarity without haze formation. They are chemically and physically stable for extended periods of time. In other words, the ketoprofen tends not to chemically react with anything either inside or outside the liquid medium. It remains dispersed and suspended in the medium and does not settle to the bottom of the container in which the composition is stored. For all intents and purposes, liquid ketoprofen compositions in accordance with this invention are stable aqueous solutions of the alkali metal salt of ketoprofen, something which Applicant is unaware of actually having been produced before. No particulate matter is evident under visual inspection and ketoprofen is uniformly dispersed and suspended in the aqueous medium. This condition is maintained for extended periods of time.

No hydrophilic emulsifying agents and colloidal clays are required to produce these compositions, nor are any special antioxidants required, such as metabisulfites, which some have claimed may cause allergic reactions in children. Also, it is not critical that pH be controlled.

Compositions in accordance with this example of the invention may be prepared by the following detailed process. First, a predetermined amount of water is measured into a vessel, which is then heated to a temperature which will aid in the dispersal of the ingredients in the liquid medium, for example 55° C. to 65° C. Then, a predetermined amount of alkali metal bicarbonate, such as potassium bicarbonate, is measured and slowly added to the heated water while it is being stirred. After the bicarbonate has been dissolved, then a predetermined amount of ketoprofen powder is slowly added to the tank while the contents of the tank are being stirred. This processing generally creates a frothy and cloudy mixture. This condition can be eliminated by allowing the tank to stand until the froth subsides. The mixture then should be stirred again and allowed to stand until it becomes clear.

At this point, it would be possible to evaporate the water in the mixture to obtain a solid crystalline alkali metal salt of ketoprofen which can be used to create solid or semi-solid dosage forms of ketoprofen If a combination product is being created, additional active ingredients may be added to the mixture at this time. For example, one or more, narcotics, antihistimines, anti-infectives, antibiotics, decongestants, or other medications can be added after the reaction between the ketoprofen composition and bicarbonate composition is complete. For example, after the ketoprofen-bicarbonate reaction takes place, a predetermined amount of hydrocodone can be added to the tank while the solution is being stirred.

Applicant has found that use of ketoprofen and potassium bicarbonate in a 2.5 grams of ketoprofen for each gram of potassium bicarbonate ratio minimizes the amount of foam and cloudiness in the mixture and minimizes the amount of time needed for these conditions to disappear.

When the foam and cloudiness have disappeared, the process may then be continued by adding sorbitol. The mixture then is stirred until the sorbitol completely disperses in the solution. If glycerin or any other excipients are used it would be added at this time until completely dispersed. Other excipients include microcrystalline cellulose, gums, and other ingredients.

Sodium benzoate in an amount that achieves a desired anti-microbial effect, or an equivalent anti-microbial agent such as one or more of butyl paraben, methyl paraben, and propyl paraben, then may be dissolved in a separate vessel. It should be noted however, that in previous studies of propionic acid compositions, the inventor found that sodium benzoate is an excipient of choice over the methyl and propyl parabens due their loss of potency over time. The anti-microbial solution then would be added to the liquid ketoprofen while stirringgl The next step would be to cool down the solution and add any additional flavoring agents while mixing.

Before preparing the composition, the preparation area should be checked for cleanliness, including all equipment coming in contact with the ingredients. In addition to the raw materials listed above, a heated jacketed tank, a transfer pump with hoses, and a filtration system should also be available. To avoid microbial contamination, contact of the ingredients and the equipment with the hands should be avoided. The purified water is placed in the heated jacketed tank which has been fitted with the proper stirring mechanism.

A clear, stable, and palatable liquid ketoprofen composition having an amount of ketoprofen salt which is the mass equivalent of about 12.5 mgs to about 150 mgs of ketoprofen per 5 mls sample may be prepared by the process described above. Liquid ketoprofen compositions having other amounts of ketoprofen salt may also be prepared.

EXAMPLE 1

A 1 liter batch of a liquid ketoprofen composition in accordance with the invention of this application may be prepared in accordance with the processing described below. The resulting composition will contain an amount of ketoprofen salt having a mass equivalent of about 25 mg of ketoprofen per 5 ml (about two tablespoons). The same procedure can be followed to obtain illustrative 12.5 mgs, 50 mgs, 100 mgs, and 150 mgs dosages, taking into consideration the calculation differential in which each ingredient will be increased/decreased accordingly. A list of the ingredients needed for the preparation of this batch is as follows:

| Ingredient | Quantity |
| --- | --- |
| Potassium bicarbonate | 2 g |
| Ketoprofen | 5 g |
| Sorbitol | 650 g |
| Butyl Paraben | Allowable amount |
| Glycerin | 5 g |
| Flavoring Systems | Allowable amount |
| Purified Water | 100 g |
| Purified Water | q.s. |

Procedure:
1. In a vessel weigh out water and heat to 55° C. to 65° C.; weigh out potassium bicarbonate and add to heated water and mix until completely dissolved;
2. Weigh out ketoprofen and add to step 1; mix until foaming subsides and clear solution is formed;
3. Allow for the solution to cool down and add sorbitol to step 1;
4. In a separate vessel weigh out glycerin and heat to 60° C.;
5. Weigh out butyl paraben and add to step 4, slowly while mixing;
6. Add step 4 to step 3;
7. Weigh out flavoring system and add to step 3; and
8. Q.S. with water.

EXAMPLE 2

A 1 liter batch of a liquid ketoprofen composition in accordance with the invention of this application may be prepared in accordance with the processing described above. The resulting composition will contain an amount of ketoprofen salt having a mass equivalent of about 25 mg of ketoprofen per 2.5 ml (about one tablespoon). The same procedure can be followed to obtain illustrative 12.5 mgs, 50 mgs, 100 mgs, and 150 mgs dosages, taking in consideration the calculation differential in which each ingredient will be increased/decreased accordingly. A list of the ingredients needed for the preparation of this batch is as follows:

| Ingredient | Quantity |
| --- | --- |
| Potassium bicarbonate | 4 g |
| Ketoprofen | 10 g |
| Sorbitol | 650 g |
| Butyl Paraben | Allowable amount |
| Glycerin | 5 g |
| Flavoring Systems | Allowable amount |
| Purified Water | 100 g |
| Purified Water | q.s. |

Procedure:
1. In a vessel weigh out water and heat to 55° C. to 65° C.; weigh out potassium bicarbonate and add to heated water and mix until completely dissolved;
2. Weigh out ketoprofen and add to step 1; mix until foaming subsides and clear solution is formed;
3. Allow the solution to cool down and add sorbitol to step 1;
4. In a separate vessel weigh out glycerin and heat to 60° C.;
5. Weigh out butyl paraben and add slowly to step 4 while mixing;
6. Add step 4 to step 3;
7. Weigh out flavoring system and add to step 3; and
8. Q.S. with water.

EXAMPLE 3

A 1 liter batch of a liquid ketoprofen composition in accordance with the invention of this application may be prepared in accordance with the processing described below. The resulting composition will contain an amount of ketoprofen salt having a mass equivalent of about 25 mg of ketoprofen per 5 ml (about two tablespoons). A list of the ingredients needed for the preparation of this batch is as follows:

| Ingredient | Quantity |
| --- | --- |
| Potassium bicarbonate | 2 g |
| Ketoprofen | 5 g |
| Sorbitol | 650 g |
| Sodium Benzoate | Allowable amount |
| Glycerin | 5 g |
| Flavoring Sytems | Allowable amount |
| Purified Water | 100 g |
| Purified Water | q.s. |

Procedure:
1. In a vessel weigh out water and heat to 55° C. to 65° C.; weigh out potassium bicarbonate and add to heated water and mix until completely dissolved;
2. Weigh out ketoprofen and add to step 1; mix until foaming subsides and clear solution is formed;
3. Allow the solution to cool down and add sorbitol to step 1;
4. In a separate vessel, weigh out glycerin and heat to 60° C.;
5. Weigh out sodium benzoate and add slowly to step 4 while mixing;
6. Add step 4 to step 3;
7. Weigh out flavoring system and add to step 3; and
8. Q.S. with water.

EXAMPLE 4

A 1 liter batch of a liquid ketoprofen composition in accordance with the invention of this application may be prepared in accordance with the processing described below. The resulting composition will contain an amount of ketoprofen salt having a mass equivalent of about 25 mg of ketoprofen per 5 ml (about two tablespoons). A list of the ingredients needed for the preparation of this batch is as follows:

| Ingredient | Quantity |
| --- | --- |
| Potassium bicarbonate | 2 g |
| Ketoprofen | 5 g |
| Sugar/other sweetening agents | 650 g |
| Sodium Benzoate | Allowable amount |
| Glycerin | 5 g |
| Flavoring Systems | Allowable amount |
| Purified Water | 100 g |
| Purified Water | q.s. |

Procedure:
1. In a vessel weigh out water and heat to 55° C. to 65° C.; weigh out potassium bicarbonate and add to heated water and mix until completely dissolved;
2. Weigh out ketoprofen and add to step 1; mix until foaming subsides and clear solution is formed;
3. Add sugar and/or other sweetening agents to step 1 while mixing
4. Allow the solution to cool down;
5. In a separate vessel, weigh out glycerin and heat to 60° C.;
6. Weigh out sodium benzoate and slowly add to step 5 while mixing;
7. Add step 5 to step 4;
8. Weigh out flavoring system and add to step 4; and
9. Q.S. with water.

EXAMPLE 5

A 1 liter batch of a liquid ketoprofen composition in accordance with the invention of this application may be prepared in accordance with the processing described below. The resulting composition will contain an amount of ketoprofen salt having a mass equivalent of about 25 mg of ketoprofen per 5 ml A list of the ingredients needed for the preparation of this batch is as follows:

| Ingredient | Quantity |
| --- | --- |
| Potassium bicarbonate | 2 g |
| Ketoprofen | 5 g |
| Sorbitol | 650 g |
| Other approved anti-microbial agents | Allowable amount |
| Glycerin | 5 g |
| Flavoring Systems | Allowable amount |
| Purified Water | 100 g |
| Purified Water | q.s. |

Procedure:
1. In a vessel weigh out water and heat to 55° C. to 65° C.; weigh out potassium bicarbonate and add to heated water and mix until completely dissolved;
2. Weigh out ketoprofen and add to step 1; mix until foaming subsides and clear solution is formed;
3. Allow the solution to cool down and add sorbitol to step 1;
4. In a separate vessel weigh out glycerin and heat to 60° C.;
5. Weigh out antimicrobial agent and add slowly to step 4 while mixing;
6. Add step 4 to step 3;
7. Weigh out flavoring system and add to step 3; and
8. Q.S. with water.

EXAMPLE 6

A 1 liter batch of a liquid ketoprofen-narcotic composition in accordance with the invention of this application may be prepared in accordance with the processing described below. The resulting composition will contain an amount of ketoprofen salt having a mass equivalent of about 25 mg of ketoprofen and 7.5 mg of hydrocodone per 5 ml (about two tablespoons). A list of the ingredients needed for the preparation of this batch is as follows:

| Ingredient | Quantity |
| --- | --- |
| Potassium bicarbonate | 2 g |
| Ketoprofen | 5 g |
| Hydrocodone | 7.5 g |
| Sorbitol | 650 g |
| Other approved anti-microbial agents | Allowable amount |
| Glycerin | 5 g |
| Flavoring Systems | Allowable amount |
| Purified Water | 100 g |
| Purified Water | q.s. |

Procedure:
1. In a vessel weigh out water and heat to 55° C. to 65° C.; weigh out potassium bicarbonate and add to heated water and mix until completely dissolved;
2. Weigh out ketoprofen and add to step 1; mix until foaming subsides and clear solution is formed;
3. Allow the solution to cool down and weigh out and add hydrocodone to step 1, while stiring until completely dissolved;
4. Weigh out sorbitol and add to step 1;
5. In a separate vessel, weigh out glycerin and heat to 60° C.;
6. Weigh out antimicrobial agent and add slowly to step 5 while mixing;
7. Add step 5 to step 4;
8. Weigh out flavoring system and add to step 4; and
9. Q.S. with water.

The following examples demonstrate additional dosage forms that can be prepared in accordance with the principles of this invention.

EXAMPLE 7

A batch of ketoprofen semi-solid composition in the form of a cream can be prepared using the following ingredients and procedures.

Oil Fraction

| Ingredient | Quantity |
| --- | --- |
| Euthanol G | 150 ml |
| Lanette O | 50 g |
| Ketoprofen | 25 g |

Water Fraction

| Ingredient | Quantity |
| --- | --- |
| Emulgin B2 | 2.5 g |
| Methyl Paraben | 0.9 g |
| Propyl Paraben | 0.1 g |
| Sorbitol | 15 g |
| Purified Water | 500 g |
| Purified Water | q.s. |

Procedure:
1. Weigh out Euthanol G and Lanette O and heat to 70 degrees Celsius;
2. Weigh out ketoprofen and add to step 1;
3. In a separate vessel, weigh out 200 g of water and heat to 70 degrees Celsius; while stirring, add the next ingredients as follows;
4. Weigh out Emulgin B2 and add to step 3;
5. Weigh out methyl and propyl paraben and add to step 3;
6. Weigh out sorbitol and add to step 3;
7. Add the water fraction to step 3, while stirring;
8. QS with water; and
9. Cool down the resulting emulsion to 25 degrees Celsius and pour into jars.

EXAMPLE 8

A batch of ketoprofen semi-solid composition in the form of gel can be prepared using the following ingredients and procedures.

| Ingredient | Quantity |
| --- | --- |
| Carbowax 540 Blend | 780 g |
| Ketoprofen | 180 g |
| Water | 30 g |
| Sodium Benzoate | 10 g |

Procedure:
1. Weigh out Carbowax 540 Blend and heat to 65° C.–70° C.;

2. Reduce heat in step 1 to 55° C. to 65° C. and add ketoprofen while mixing;
3. Weigh out Sodium Benzoate and add to step 2;
4. Weigh out water while mixing add to step 3; and
5. Pour into gel tubes and let set until gel is formed

EXAMPLE 9

A batch of ketoprofen semi-solid composition in the form of a suppository can be prepared using the following ingredients and procedures.

| Ingredient | Quantity |
| --- | --- |
| PEG 8000 Powder | 1.2 g |
| PEG 400 Liquid | 1.0 g |
| Ketoprofen | Predetermined dose amount |

Note:
Dose amount could be 12.5 mgs; 25 mgs; 50 mgs; 75 mgs

Procedure:
1. Stir PEG 8000 into PEG 400;
2. Heat in a water jacketed vessel or water bath and heat until PEG 400 liquifies;
3. While mixing add a predetermined amount of ketoprofen;
4. While in liquid state pour into designated molds; and
5. Let cool in molds at room temperature before removing formed suppositories.

EXAMPLE 10

A 1 liter batch of a water-soluble ketoprofen composition for a mass equivalent 25 mg of ketoprofen per 1 ml injectable dose can be prepared using the following ingredients and procedures.

| Ingredient | Quantity |
| --- | --- |
| Potassium Bicarbonate | 10 g |
| Ketoprofen | 25 g |
| Sterile Water for injection | 500 g |
| Sterile Water for injection | q.s. |

Note:
Dose amount could be 12.5 mgs; 25 mgs; 50 mgs; 75 mgs; 100 mgs; 150 mgs

Procedure:
1. Weigh out water and heat to 55° C. to 65° C.; weigh out potassium bicarbonate and add to heated water and mix until dissolved;
2. Weigh out ketoprofen and add to step 1; mix until foaming subsides and a clear solution forms; and
3. Q.S. with water.

EXAMPLE 11

A 1 liter batch of solvent-based ketoprofen composition for a 25 mg per 1 ml injectable dose can be prepared using the following ingredients and procedures.

| Ingredient | Quantity |
| --- | --- |
| PEG 300 | 255 g |
| Sorbitol 70% solution | 100 g |
| Ethyl Alcohol | 55 g |
| Ketoprofen | 25 g |
| Sterile Water for injection | 500 g |
| Sterile Water for injection | q.s. |

Note:
Dose amount could be 12.5 mgs; 25 mgs; 50 mgs; 75 mgs; 100 mgs; 150 mgs

Procedure:
1. Weigh out PEG 300 and sorbitol and mix together;
2. In a separate vessel, weigh out ethyl alcohol;
3. Weigh out ketoprofen and add to step 2;
4. Add step 1 to step 3 while mixing; and
5. Q.S. with water.

EXAMPLE 12

A 1 liter batch of a water-soluble ketoprofen composition for a 7.5 mg of hydrocodone and a mass equivalent of 25 mg of ketoprofen per 1 ml injectable dose can be prepared using the following ingredients and procedures.

| Ingredient | Quantity |
| --- | --- |
| Potassium Bicarbonate | 10 g |
| Ketoprofen | 25 g |
| Hydrocodone | 7.5 g |
| Sterile Water for injection | 500 g |
| Sterile Water for injection | q.s. |

Note:
Dose amount for ketoprofen could be 12.5 mgs; 25 mgs; 50 mgs; 75 mgs; 100 mgs; 150 mgs
Dose amount of hydrocodone could be 7.5 mgs or higher.

Procedure:
1. Weigh out water and heat to 55° C. to 65° C.; weigh out potassium bicarbonate and add to heated water and mix until dissolved;
2. Weigh out ketoprofen and add to step 1; mix until foaming subsides and a clear solution forms;
3. Allow for solution to cool down and add the hydrocodone while stirring until completely dissolved.
4. Q.S. with water.

EXAMPLE 13

A 1 liter batch of a liquid ketoprofen-narcotic composition in accordance with the invention of this application may be prepared in accordance with the processing described below. The resulting composition will contain about 25 mg of ketoprofen and 7.5 mg of hydrocodone per 1 ml A list of the ingredients needed for the preparation of this batch is as follows:

| Ingredient | Quantity |
| --- | --- |
| PEG 300 | 255 g |
| Sorbitol 70% solution | 100 g |
| Ethyl Alcohol | 55 g |

-continued

| Ingredient | Quantity |
| --- | --- |
| Ketoprofen | 25 g |
| Hydrocodone | 7.5 g |
| Sterile Water for injection | 500 g |
| Sterile Water for injection | q.s. |

Note:
Dose amount of ketoprofen could be 12.5 mgs; 25 mgs; 50 mgs; 75 mgs; 100 mgs; 150 mgs
Dose amount of hydrocodone could be 7.5 mgs or higher.

Procedure:
1. Weigh out PEG 300 and sorbitol and mix together;
2. In a separate vessel weigh out ethyl alcohol;
3. Weigh out ketoprofen and add to step 2, while stirring;
4. Weight out hydrocodone and add to step 3 while stirring;
5. Add step 1 to step 3 while mixing; and
6. Q.S. with water.

The invention claimed is:

1. A liquid ketoprofen composition consisting of a ketoprofen composition and potassium bicarbonate dissolved in an aqueous medium in a gram ratio of 2.5 grams of ketoprofen composition to 1 gram of potassium bicarbonate, the liquid composition being prepared by a process comprising the steps of dissolving potassium bicarbonate in an aqueous medium and dissolving a therapeutically effective amount of ketoprofen composition in the aqueous medium so that no particulate matter is evident in the liquid composition upon visual examination.

* * * * *